(12) United States Patent
Tanoue et al.

(10) Patent No.: US 7,903,248 B2
(45) Date of Patent: Mar. 8, 2011

(54) LUMINESCENCE MEASURING APPARATUS

(75) Inventors: Hidetsugu Tanoue, Hitachinaka (JP);
Masato Ishizawa, Hitachinaka (JP);
Yoichiro Suzuki, Mito (JP)

(73) Assignee: Hitachi High-Technologies Corporation, Tokyo (JP)

( * ) Notice: Subject to any disclaimer, the term of this patent is extended or adjusted under 35 U.S.C. 154(b) by 280 days.

(21) Appl. No.: 12/037,644

(22) Filed: Feb. 26, 2008

(65) Prior Publication Data
US 2008/0225279 A1    Sep. 18, 2008

(30) Foreign Application Priority Data

Feb. 28, 2007 (JP) .................................. 2007-048382

(51) Int. Cl.
*G01N 21/25* (2006.01)
(52) U.S. Cl. ........................................................ 356/417
(58) Field of Classification Search .................. 356/417, 356/317–318; 250/361 C; 422/52
See application file for complete search history.

(56) References Cited

U.S. PATENT DOCUMENTS

| | | | | | |
|---|---|---|---|---|---|
| 3,764,214 | A | * | 10/1973 | Heiss ........................... | 250/458.1 |
| 3,861,788 | A | * | 1/1975 | Webster ........................ | 356/418 |
| 4,319,842 | A | * | 3/1982 | Priarone et al. ............... | 356/317 |
| 4,536,655 | A | * | 8/1985 | Barnes ......................... | 250/461.1 |
| 5,082,628 | A | | 1/1992 | Andreotti et al. | |
| 5,086,233 | A | * | 2/1992 | Stafford et al. ............. | 250/458.1 |
| 5,371,350 | A | * | 12/1994 | Motolese .................... | 250/361 C |
| 6,268,218 | B1 | * | 7/2001 | Pantoliano et al. ........... | 436/172 |
| 6,317,206 | B1 | * | 11/2001 | Wulf ........................... | 250/458.1 |
| 6,844,965 | B1 | * | 1/2005 | Engelhardt .................. | 250/458.1 |
| 2002/0179835 | A1 | * | 12/2002 | Feygin ......................... | 250/332 |
| 2004/0159798 | A1 | * | 8/2004 | Martin et al. ............... | 250/458.1 |
| 2006/0057710 | A1 | * | 3/2006 | Ishiura et al. ................ | 435/287.3 |

FOREIGN PATENT DOCUMENTS

| | | |
|---|---|---|
| EP | 1 319 941 | 6/2003 |
| JP | 2000-146825 | 5/2000 |
| JP | 2002-310894 | 10/2002 |
| JP | 2004-003888 | 1/2004 |
| KR | 2004-0108467 | 12/2004 |

* cited by examiner

*Primary Examiner* — Kara E Geisel
(74) *Attorney, Agent, or Firm* — Mattingly & Malur, P.C.

(57) ABSTRACT

To increase the direct light received by the detector and decrease reflections from the detection component support structures, the luminescent substance is placed as close to the detector as possible. More specifically, the apparatus is configured so as to slide out a structure shielding the detector from light and at the same time slide in the vessel containing the luminescent substance therein until the vessel comes right under the detector. The invention can detect trace luminescence from a small-volume sample by maximizing the amount of direct light received from the sample and minimizing the decay of indirect light received from the sample attributable to interactions with the vessel for containing the sample therein, the structure for collecting light, and the structure for supporting other detection components.

3 Claims, 3 Drawing Sheets

LUMINESCENCE MEASURING APPARATUS

BACKGROUND OF THE INVENTION

1. Field of the Invention

The present invention relates to an apparatus which quantifies faint fluorescent or phosphorescent luminescence which is biologically, chemically or electrochemically generated. In particular, the invention relates to a luminescence measuring apparatus which uses a photomultiplier tube for measurement.

2. Description of the Related Art

As a qualitative/quantitative analysis technique, it is known to use a substance which specifically binds to a constituent of the object to be assayed. The substance is labeled, and the constituent is identified and quantified by measuring the label. This technique is particularly effective when the amount of the constituent of interest is very small and therefore has been used in determining the presence or absence of antigens, antibodies, enzymes and particular genetic sequences in biological samples. In the past, a radioactive substance or the like was used as the label. However, since the radioactive substance cannot easily be handled due to the radioactivity and other problems, it has recently become common to use a luminescent substance as the label. The luminescent substance is such a bioluminescent substance as in a firefly or a chemiluminescent substance. Immediately before luminescence measurement is performed, a trigger substance is added to induce bioluminescence or chemiluminescence. For example, bioluminescence occurs when an enzyme-containing liquid is mixed with a liquid which contains the corresponding substrate since the substrate is oxidized by the enzyme and therefore excited to an active state resulting in luminescence. Whereas the amount of luminescence is proportional to the amount of the substrate, the amount of the substrate emitting luminescence is dependent on the concentration of the enzyme. Accordingly, it is possible to indirectly quantify the amount of the enzyme by measuring the amount of luminescence.

Conventional trace-fluorescence measuring apparatuses are such that a luminescent substance is put in a vessel shaped to have a larger height than the bottom and a detector is arranged to face the side or bottom of the tube-shaped vessel, allowing the measuring tool to measure the light emitted from the luminescent substance. Whether the detector is arranged to face the tube's side or bottom, a light reflector is set opposite to the measuring tool so that faint light can be detected. In this case, direct light escapes through a hole of the light reflector which is formed as part of the structure necessary to hold the tube. In addition, even if the structure to hold the tube is designed not to require the light reflector to have such a hole, light impinges on the structure resulting in a decrease in light intensity. Furthermore, light from the luminescent substance considerably decreases or decays in intensity before reaching the detector due to scattering and absorption during transmission through the liquid and the tube's wall.

In the case of the trace-luminescence measuring apparatus described in JP-A-2000-146825, when a test tube with a substance to be measured therein included is inserted, a shutter unit provided for the light reception unit is forced to move, allowing the light reception unit to directly receive light from the substance.

SUMMARY OF THE INVENTION

The method described in Patent Document is implemented by a simple configuration. However, since a sample is contained in a cylindrical test tube, the method has a problem that the light emission area (light reception area) is limited. More specifically, although the sample should have a thin and flat shape parallel to the light reception surface in order to maximize the amount of luminescence measured, this point is not considered in the technique described in JP-A-2000-146825.

It is an object of the present invention to provide a luminescence measuring apparatus enabled to detect trace luminescence from a small-volume sample by maximizing the amount of direct light received from the sample and minimizing the decay of indirect light received from the sample attributable to interactions with the vessel for containing the sample therein, the structure for collecting light, and the structure for supporting other detection components.

To achieve the object mentioned above, the present invention configures a luminescence measuring apparatus as follows.

A luminescence measuring apparatus comprises: a vessel for containing a luminescent-substance-included sample; and a detector section for converting light emitted from the luminescent substance into an electric signal by a detector opposed to the vessel, wherein a vessel holding section for holding the vessel is independent of a detector holding section for holding the detector, the luminescence measuring apparatus further including means for causing relative displacement of either the vessel holding section or the detector holding section.

In other words, the luminescence measuring apparatus is provided with a mechanism which slides out a structure shielding the detector from light and at the same time slides in the vessel containing the luminescent substance therein until the vessel comes right under the detector.

This configuration makes it possible to place the luminescent substance nearest to the detector. This increases the direct light received by the detector while decreasing reflection by the structure provided to support detection components. It is also possible to use such a low-height vessel having an opening on its upper face in which the luminescent-substance-included fluid contained in the vessel is distributed thinly or substantially as widely as the effective area of the detector. This increases the direct light received by the detector while decreasing the decay of light in intensity due to propagation through the fluid and the vessel. In addition, a reflector may be disposed below a transparent vessel so that the light emitted in the opposite direction of the detector is reflected toward the detector. It is also possible to dispose reflectors on lateral sides of the vessel so that the light emitted toward the vessel's lateral sides is reflected toward the detector. In either case, more indirect light is gathered to the detector. Thus, direct light and indirect light from the luminescent substance can effectively be introduced to the detector to realize higher measurement sensitivity.

Since the vessel containing the luminescent substance therein has an opening facing the measuring tool, direct light is effectively incident on the detector, thus raising the sensitivity. The luminescent substance is also placed near the detector. This raises the sensitivity, too. By adding reflectors, light emitted not in the direction of the detector may effectively be retrieved and used. This raises the sensitivity as well.

DETAILED DESCRIPTION OF THE PREFERRED EMBODIMENTS

The present invention will be described below in detail by way of embodiments.

First Embodiment

Figure 1:
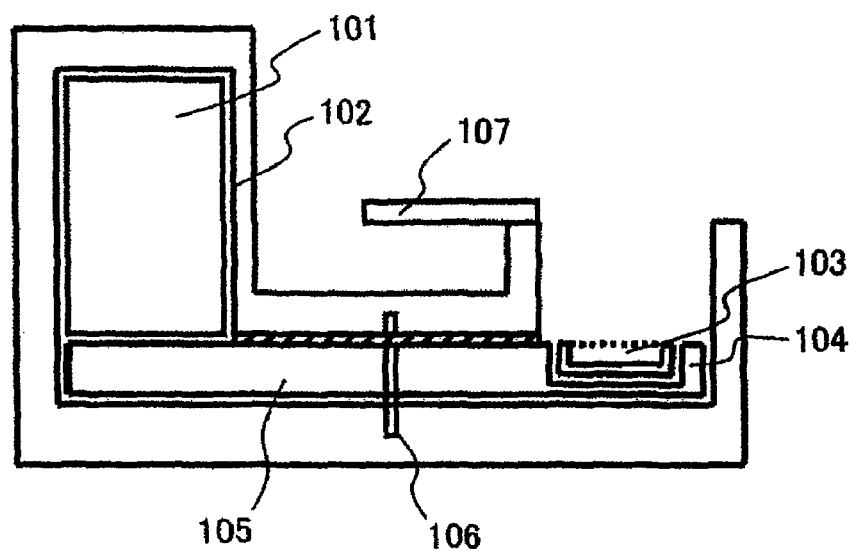
FIGS. 1A-1B illustrate a first embodiment of the present invention.
Figure 1:
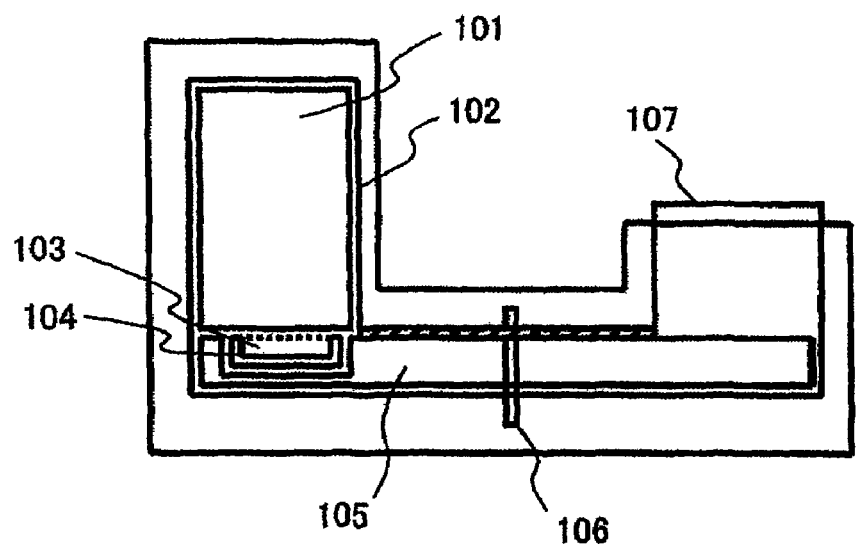

FIGS. 1A and 1B show a first embodiment of the present invention. In FIG. 1A, measurement is not being performed. In FIG. 1B, measurement is being performed.

According to the present invention, a detector 101 is installed inside a dark room 102 as shown in FIG. 1A. A fluid 103 including a luminescent substance is contained in a vessel 104. With a cover 107 opened, the vessel 104 is set on a vessel carrier 105 which can be rotated by a rotation axis 106. By a part of the surface of the vessel carrier 105, the detector 101 remains shielded from external light.

To perform measurement, the cover 107 is closed as shown in FIG. 1B. Then, the rotation axis 106 is spun to rotate the vessel carrier 105 and slides the luminescent-substance-included fluid 103 contained in the vessel 104 set on the vessel carrier 105 until the fluid 103 comes right under the detector 101. Under this condition allowing the detector 101 to receive light only from the luminescent substance, the amount of luminescence is measured by the detector 101.

Second Embodiment

Figure 2:
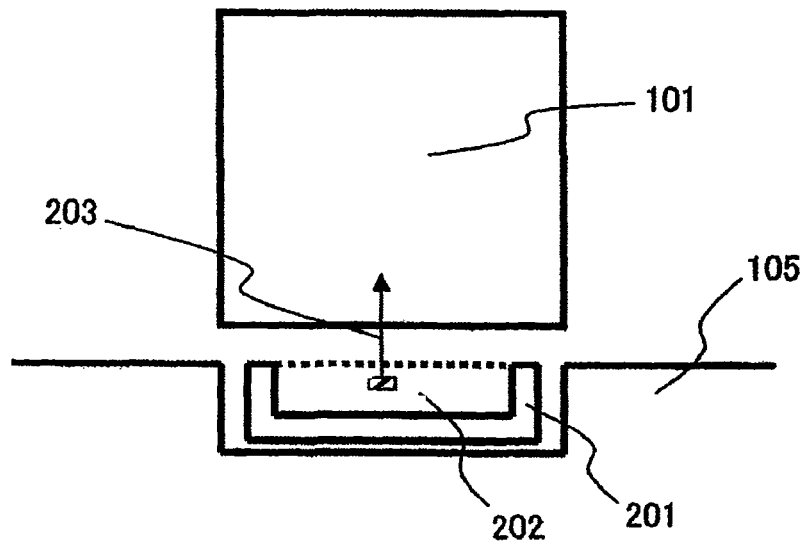
FIG. 2 illustrates a second embodiment of the present invention.

FIG. 2 illustrates a second embodiment of the present invention. It shows how the opening of the vessel is disposed relative to the detector when measurement is being performed. The detector 101 detects light 203 from a luminescent-substance-included fluid 202 contained in a vessel 201 held by the vessel carrier 105. Since the opening of the vessel 201 faces the detector 101, the light 203 does not propagate through the vessel 201 and therefore does not decay in intensity. The detector 101 shows high measurement sensitivity since such incident light 203 is detected.

Third Embodiment

Figure 3:
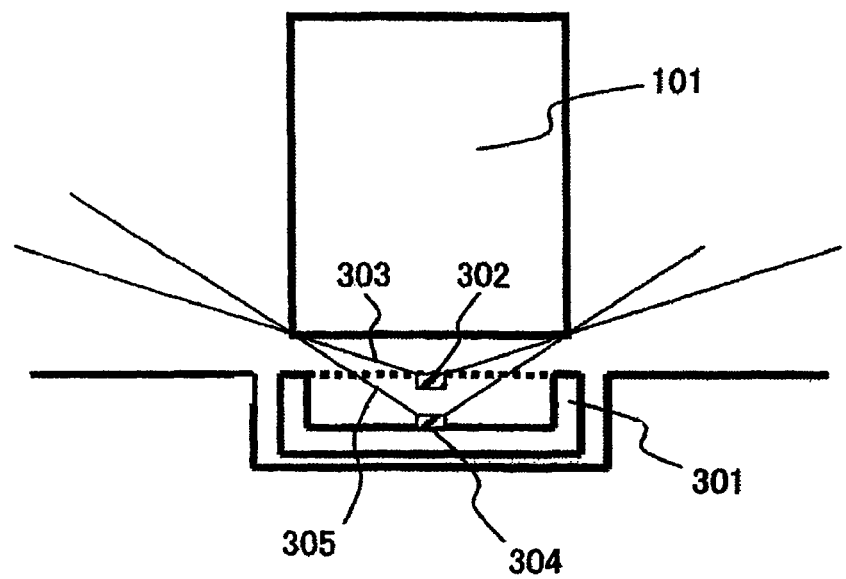
FIG. 3 illustrates a third embodiment of the present invention.

FIG. 3 illustrates a third embodiment of the present invention. It shows how direct light from the luminescent-substance-included fluid in the vessel is received by the detector when measurement is being performed. The range 1 303 of direct light incident on the detector 101 from a luminescent substance 1 (302) in a vessel 301 is wider than the range 2 (305) of direct light incident on the detector 101 from a luminescent substance 2 (304) which is farther from the detector 101 than the luminescent substance 1 (302). In terms of the amounts of direct light, this means that the detector receives more light from the luminescent substance 1 (302) that is located closer to the detector than from the luminescent substance 2 (304) that is located farther from the detector.

Thus, it is possible to detect more direct light by forming the vessel so that the luminescent-substance-included fluid contained therein is located nearer to a measuring tool and scattered more thinly or substantially as widely as the light reception area of the detector.

For example, assume that a luminescent-substance-included 50 ul fluid is to be measured. In this case, if the light reception area of the detector is 25 mm in diameter, an ideal vessel is a 25-mm-diameter one with an inner wall height of 0.1 mm. In the case of a tube with a capacity of about 200 ul, it has an opening diameter of about 6 mm. According to a simple comparison between their opening diameters or open areas, it is possible to receive about 17 times more direct light from the ideal vessel than from the tube.

Fourth Embodiment

Figure 4:
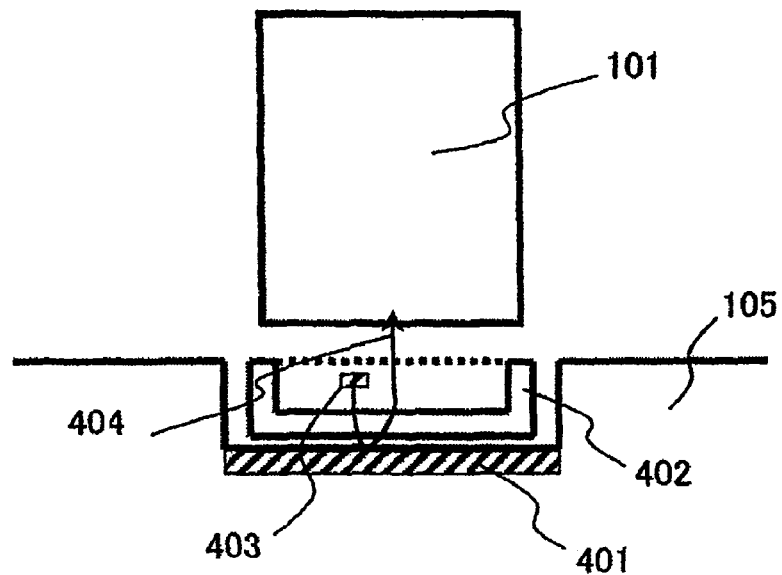
FIG. 4 illustrates a fourth embodiment of the present invention.

FIG. 4 illustrates a fourth embodiment of the present invention. As shown in FIG. 4, when measurement is being performed, light from the luminescent-substance-included fluid is retrieved by a reflector disposed at the opposite side of the vessel as viewed from the measuring tool.

Light 404, which is produced from a luminescent substance 403 in a vessel 402 held by the vessel carrier 105 and emitted in the opposite direction of the detector 101, is reflected toward the detector 101 by a reflector 401. This reflector makes it possible to retrieve light which is emitted from the luminescent substance in the opposite direction of the detector. Therefore, indirect light from the luminescent substance can be detected effectively, resulting in an improved sensitivity.

Preferably, the reflector is shaped to be parallel with the bottom of the vessel. For example, if the vessel has a flat bottom as in the third embodiment, the reflector is shaped to have a flat surface on the measuring-tool side.

It is preferable to realize a reflectivity of almost 100%. Known sheet-type reflecting films can provide a reflectivity of 95% or higher. The reflectivity obtained by those reflectors subjected to aluminum vapor deposition is about 80%.

If the reflector is flat, the reflector may be formed either by using a sheet-type film or by performing aluminum vapor deposition. In the case of a curved reflector, however, it is difficult to use a sheet-type film.

It is therefore preferable to employ a flat reflector if a reflector with a high reflectivity is to be selected.

Fifth Embodiment

Figure 5:
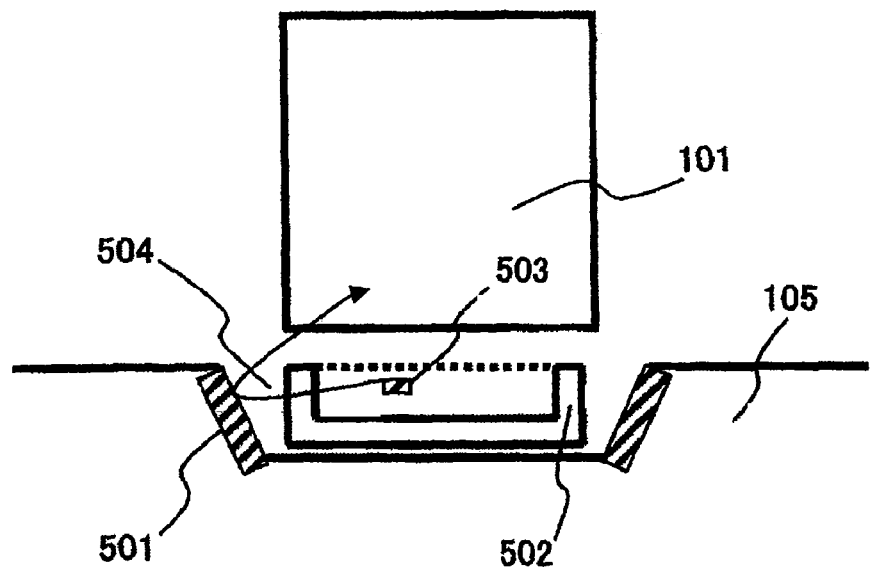
FIG. 5 illustrates a fifth embodiment of the present invention.

FIG. 5 illustrates a fifth embodiment of the present invention. When measurement is being performed, as shown in FIG. 5, light from the luminescent substance is retrieved by reflectors disposed on lateral sides of the vessel.

Light 504, which is produced from a luminescent substance 503 in a vessel 502 held by the vessel carrier 105 and emitted toward the lateral sides of the vessel 502, is reflected toward the detector 101 by a reflector 501. This reflector makes it possible to retrieve light which is emitted toward the lateral sides of the vessel 502. Therefore, indirect light from the luminescent substance can be detected effectively, resulting in an improved sensitivity.

What is claimed is:
1. A luminescence measuring apparatus comprising:
a housing in which a vessel carrier is rotatably mounted;
a vessel for containing a luminescent-substance-included sample;
said vessel carrier including a vessel holding section for holding the vessel;
a detector section mounted within the housing for converting light emitted from a luminescent substance into an electric signal by a detector opposed to the vessel; and
the vessel having an opening facing the detector, wherein the detector section comprises a darkroom and holds the detector;

an upper side of the vessel carrier, in conjunction with the housing, shields external light from the interior of the detector section; and said housing has an opening section that allows the vessel to be placed in or removed from the vessel carrier;

the opening section and the detector section are separated from each other;

the opening section includes a cover that covers and uncovers a part of the upper side of the vessel carrier; and the vessel carrier rotates, to transport the vessel between the opening section and the detector section.

2. The luminescence measuring apparatus according to claim 1, wherein the vessel is shaped so that the luminescent-substance-included sample contained therein is distributed thinly and substantially as widely as the light reception area of the detector.

3. The luminescence measuring apparatus according to claim 1, further comprising a reflector by which light emitted from the vessel not in the direction of the detector is reflected toward the detector.

* * * * *